(12) United States Patent
Wershofen et al.

(10) Patent No.: US 8,513,453 B2
(45) Date of Patent: Aug. 20, 2013

(54) PROCESS FOR PREPARING AROMATIC CARBAMATES

(75) Inventors: Stefan Wershofen, Moenchengladbach (DE); Stephan Klein, Mettmann (DE); Anton Vidal-Ferran, Montbrio (ES); Elisenda Reixach, Torello (ES); Francese Xavier Rius-Ruiz, Tarragona (ES)

(73) Assignee: Bayer MaterialScience AG, Leverkusen (DE)

( * ) Notice: Subject to any disclaimer, the term of this patent is extended or adjusted under 35 U.S.C. 154(b) by 132 days.

(21) Appl. No.: 13/256,969

(22) PCT Filed: Mar. 12, 2010

(86) PCT No.: PCT/EP2010/001563
§ 371 (c)(1),
(2), (4) Date: Sep. 16, 2011

(87) PCT Pub. No.: WO2010/105768
PCT Pub. Date: Sep. 23, 2010

(65) Prior Publication Data
US 2012/0041223 A1 Feb. 16, 2012

(30) Foreign Application Priority Data

Mar. 16, 2009 (EP) .................................. 09003729

(51) Int. Cl.
*C07C 269/04* (2006.01)
*C07C 263/04* (2006.01)
(52) U.S. Cl.
USPC ........................................... 560/24; 560/345
(58) Field of Classification Search
USPC .................................................. 560/24, 345
See application file for complete search history.

(56) References Cited

U.S. PATENT DOCUMENTS

| 3,763,217 A | 10/1973 | Brill |
| 4,268,683 A | 5/1981 | Gurgiolo |
| 5,347,034 A | 9/1994 | Hammen et al. |

FOREIGN PATENT DOCUMENTS

| CA | 2072034 A1 | 12/1992 |
| CN | 1419538 A | 5/2003 |
| EP | 0049671 A1 | 4/1982 |
| EP | 0065026 A1 | 11/1982 |
| EP | 510459 A2 | 10/1992 |
| EP | 520273 A2 | 12/1992 |
| EP | 0752413 A1 | 1/1997 |
| EP | 0752414 A1 | 1/1997 |
| EP | 1255728 B1 | 11/2002 |
| EP | 1268409 B1 | 1/2003 |
| EP | 1958940 A1 | 8/2008 |
| WO | WO-01/56977 A1 | 8/2001 |
| WO | WO-01/68590 A1 | 9/2001 |

OTHER PUBLICATIONS

Baba, T., et al., *Catalytic Synthesis of Dimethyltoluene-2,4-dicarbamate by the Methoxycarbonylation of 2,4-Touluene Diamine with Dimethyl Carbonate Using Zn (OAc)2-2H2O*, Science and Technology in Catalysis (2002), pp. 149-152.
Baba, T., et al., *Catalytic methoxycarbonylation of aromatic diamines with dimethyl carbonate to their dicarbamates using zinc acetate*, Catalysts Letters, vol. 82, No. 3-4, pp. 193-197, Oct. 2002.
Baba, T., et al., *Characteristics of methoxycarbonylation of aromatic diamine with dimethyl carbonate to dicarbamate using a zinc acetate catalyst*, Green Chemistry, 7, pp. 159-165, 2005.
Office Action issued in China for corresponding Chinese application No. 201080012312.4, dated Mar. 4, 2013.

*Primary Examiner* — Johann R Richter
*Assistant Examiner* — Blaine G Doletski
(74) *Attorney, Agent, or Firm* — Novak Druce Connolly Bove + Quigg LLP

(57) ABSTRACT

The invention is directed to a process for preparing aromatic carbamates which comprises the reaction of an aromatic amine with an organic carbonate in the presence of a catalyst characterized in that $Zn_4O(OAc)_6$ is used as catalyst.

16 Claims, 2 Drawing Sheets

PROCESS FOR PREPARING AROMATIC CARBAMATES

CROSS-REFERENCE TO RELATED APPLICATIONS

This application is a national stage application (under 35 U.S.C. §371) of PCT/EP2010/001563, filed Mar. 12, 2010, which claims benefit of European application 09003729.2, filed Mar. 16, 2009, both of which are incorporated herein by reference in their entirety for all their useful purposes.

BACKGROUND

The present invention refers to a new process for preparing aromatic carbamates from aromatic amines and organic carbonates in the presence of a tetranuclear zinc catalyst.

Aromatic carbamates are valuable intermediates which can be used for the production of phytodrugs, dyes, pharmaceutical compounds and aromatic isocyanates used in the synthesis of polyurethanes.

Among aromatic carbamates, those of greatest interest from a commercial point of view are carbamates derived from 4,4'-methylenediphenylamine (MDA), also known as 4,4'-diaminodiphenylmethane, its isomers and/or homologues or mixtures of the aforementioned compounds as obtained by acid catalyzed condensation/rearrangement reaction of aniline and formaldehyde, as well as 2,4-toluenediamine (TDA) or technical mixtures of the two TDA isomers 2,4-TDA and 2,6-TDA (about 80/20 mixtures). The mentioned aromatic amines are used in the preparation of methylenediphenyl diisocyanate (MDI) and toluene diisocyanate (TDI). At present these isocyanates are produced industrially by phosgenation of the corresponding amines with phosgene.

In the prior art, processes are known for the production of carbamates, which are based on the functionalization of aromatic amines Ar—$NH_2$ with organic carbonates $R_2CO_3$ in the presence of suitable catalysts, according to the following scheme:

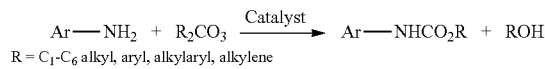

R = $C_1$-$C_6$ alkyl, aryl, alkylaryl, alkylene

In the case of aromatic diamines Ar(—$NH_2$)$_2$, biscarbamates are formed in a two step reaction, being the respective monocarbamates formed in the first step according to the following scheme:

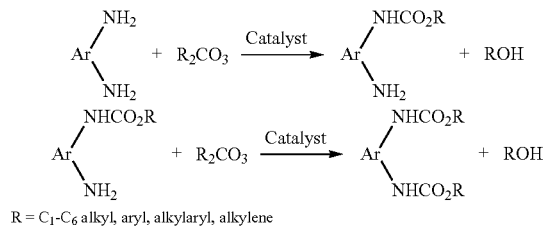

R = $C_1$-$C_6$ alkyl, aryl, alkylaryl, alkylene

Taking into account the alkylating properties of organic carbonates, N-alkylation competes with N-alkoxycarbonylation, and consequently N-alkylated products might be formed along the reaction.

In the U.S. Pat. No. 3,763,217 it is disclosed that Lewis acids are suitable catalysts for reacting an organic carbonate with an aromatic amine to prepare carbamates. The following catalysts are disclosed in that US patent: $SbCl_5$, $SbCl_3$, $SbCl_2$, $AlCl_3$, $SbF_3$, $FeCl_3$, $UO_2(NO_3)_2$, $UO_2$, $UO_3$, $NbCl_5$ and $ThCl_4$.

In the U.S. Pat. No. 4,268,683 it is disclosed that zinc and divalent tin salts of monovalent organic compounds having a pKa value of at least 2.8 provide the desired carbamates in higher yields and/or selectivity than the particular Lewis acids disclosed in the U.S. Pat. No. 3,763,217. In particular the following zinc compounds are disclosed: zinc acetate, zinc acetate dihydrate, zinc naphtenate, zinc salts of fatty acids, zinc pivalate, zinc benzoate, zinc acrylate, zinc p-chlorobenzoate, zinc phenoxide, zinc oxyacetate (($AcOZn)_2O$), zinc chloride, zinc propionate, zinc formate, zinc chloroacetate, zinc trifluoroacetate, zinc salicylate, zinc oxalate, and zinc acetylacetonate.

In the European patent application EP-A-0065026 it is disclosed a process for preparing a carbamate from an organic carbonate and an aromatic amine in the presence of catalytic quantities of a Lewis acid catalyst, which is soluble in the reaction mixture at the reaction conditions and is a member of the group consisting of a zinc or divalent tin halide, a zinc or divalent tin salt of a monovalent organic compound which has a pKa value of at least 2.8, and a zinc or divalent tin salt of trifluoroacetic acid. Among the zinc salts are mentioned: zinc chloride, zinc acetate, zinc acetate dihydrate, zinc oxyacetate (($AcOZn)_2O$), zinc naphtenate, zinc octoate, zinc propionate, zinc salicylate, zinc pivalate, zinc acrylate, zinc p-chlorobenzoate, zinc phenolate, zinc formate, zinc chloroacetate, zinc acetylacetonate, zinc oxalate, and zinc trifluoroacetate.

In the article of Baba et al., Catalytic Synthesis of Dimethyltoluene-2,4-dicarbamate by the Methoxycarbonylation of 2,4-Toluenediamine with Dimethyl Carbonate Using $Zn(OAc)_2.2H_2O$, Science and Technology in Catalysis, 2002, 149, it is disclosed the reaction of the amines MDA and TDA with dimethyl carbonate in the presence of a metal salt as catalyst to obtain the corresponding dicarbamates. Several salts of zinc, tin, lead and bismuth are disclosed. It is disclosed also that the selection of the metal salt is crucial for the formation of the carbamates. Among the catalysts some zinc carboxylates showed catalytic activity and other were inactive. For example in the reaction of TDA with dimethyl carbonate and zinc acetate dihydrate as catalyst yielded 92% of dicarbamate, zinc propionate yielded 20%, whereas zinc formate was inactive.

In the article of Baba et al., Catalytic methoxycarbonylation of aromatic diamines with dimethyl carbonate to their dicarbamates using zinc acetate, Catalysis Letters, 2002, 82(3-4), 193-197, it is disclosed the preparation of dicarbamates by methoxycarbonylation of TDA and MDA with dimethyl carbonate using zinc acetate dihydrate, $Zn(OAc)_2$.$2H_2O$, or zinc acetate, $Zn(OAc)_2$, as catalysts. The yield in the methoxycarbonylation of TDA with dimethyl carbonate using the hydrated catalyst is 92%, and using the non hydrated catalyst it is 98%. In the case of MDA the yield with zinc acetate dihydrate as catalyst is 98%.

In the article of Baba et al., Characteristics of methoxycarbonylation of aromatic diamine with dimethyl carbonate to dicarbamate using zinc acetate as catalyst, Green Chem., 2005, 7, 159-165, it is disclosed the reaction of aromatic amines, TDA and m-phenylenediamine, with dimethyl carbonate in the presence of zinc acetate dihydrate as catalyst.

EP-A-1268409 describes the usage of zinc acetate dihydrate as catalyst in a continuous process for the manufacturing of aromatic carbamates by reaction of 80/20 mixtures of the two TDA isomers 2,4-TDA and 2,6-TDA with dimethyl carbonate. Among other compounds, Zn salts (e.g. zinc acetate or zinc acetate dehydrate) are mentioned in EP-A-1255728 as catalysts for the synthesis of aromatic carbamates by reaction of aromatic amines like 80/20 mixtures of the two TDA isomers 2,4-TDA and 2,6-TDA with dimethyl carbonate.

Compounds or salts of especially Sn, Zn or Pb are described as catalysts for the reaction of 2,4-TDA or technical mixtures of the two TDA isomers 2,4-TDA and 2,6-TDA with diethyl carbonate in EP-A-520273 or for the reaction of MDA (that is 4,4'-MDA, its isomers and/or homologues or mixtures of the aforementioned compounds as obtained by acid catalyzed condensation/rearrangement reaction of aniline and formaldehyde) with dialkyl carbonates like dimethyl carbonate or diethyl carbonate in EP-A-510459.

In the European patent application EP-A-1958940, the inventors disclose processes for preparing azolynes, cyanoazolynes, symmetrical and unsymmetrical bisazolynes, amides, bisamides, cyanoamides, and peptides, which comprise the use of a metal catalyst defined by the general formula $Zn_a(OCOR7)_bZ2_c$, wherein R7 represents an optionally substituted alkyl group or an optionally substituted aryl group; Z2 represents an oxygen atom, a sulfur atom, or a selenium atom, "a" represents 1 or 4, "b" represents 2 or 6, and "c" represents 0 or 1; and provided that when "a" is 1, "b" is 2 and "c" is 0, and when "a" is 4, "b" is 6 and "c" is 1. The following zinc salts are disclosed in that patent application: zinc acetate, zinc trifluoroacetate, zinc acetoacetonate, zinc acetylacetonate, zinc trifluomethanesulfonate, and zinc p-toluenesulfonate. It is disclosed also that multinuclear zinc clusters may be used as catalysts, for example: $Zn_4(OAc)_6O$, $Zn_4(OCOEt)_6O$, $Zn_4(OPv)_6O$, $Zn_4[OCO(CH_2)_{16}CH_3]_6O$, $Zn_4(OCOPh)_6O$ and $Zn_4(OCOCF_3)_6O$, wherein Ac represents an acetyl group, Et represents an ethyl group, Pv represents a pivaloyl group, and Ph represents a phenyl group. The zinc cluster $Zn_4(OAc)_6O$ is used in the preparation of oxazolynes and peptides. However, EP-A-1958940 does not disclose or suggest the use of the aforementioned catalysts such as $Zn_4(OAc)_6O$ for the preparation of aromatic carbamates.

Taking into account the economic importance of carbamates as isocyanates precursors, it is necessary to develop new and improved alternative processes for preparing carbamates in high yield and low amounts of by-products.

BRIEF DESCRIPTION OF THE DRAWINGS

The foregoing summary, as well as the following detailed description of the invention, may be better understood when read in conjunction with the appended drawings. For the purpose of assisting in the explanation of the invention, there are shown in the drawings representative embodiments which are considered illustrative. It should be understood, however, that the invention is not limited in any manner to the precise arrangements and instrumentalities shown.

Thus, the object of the invention is to provide a new process for preparing aromatic carbamates in high yield. This object has been achieved by the provision of the process according to the invention which comprises the reaction of an aromatic amine with an organic carbonate in the presence of $Zn4O(OAc)_6$ as catalyst.

Aromatic Amines

Figure 1:
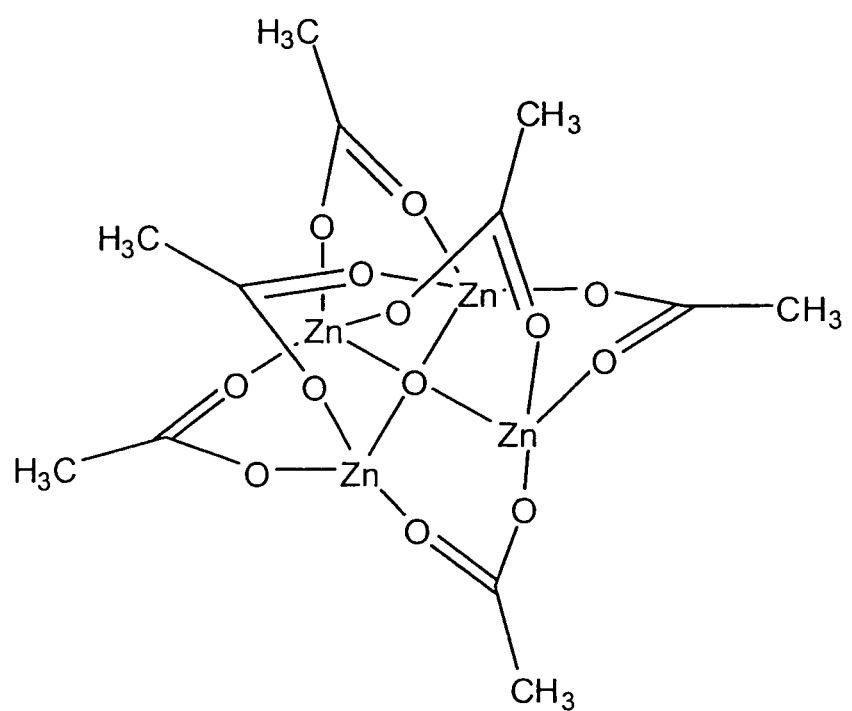

In the process of the invention the aromatic amine is preferably selected from the group of aromatic amines represented by the general formulas (I), (II), (III), (IV) and (V):

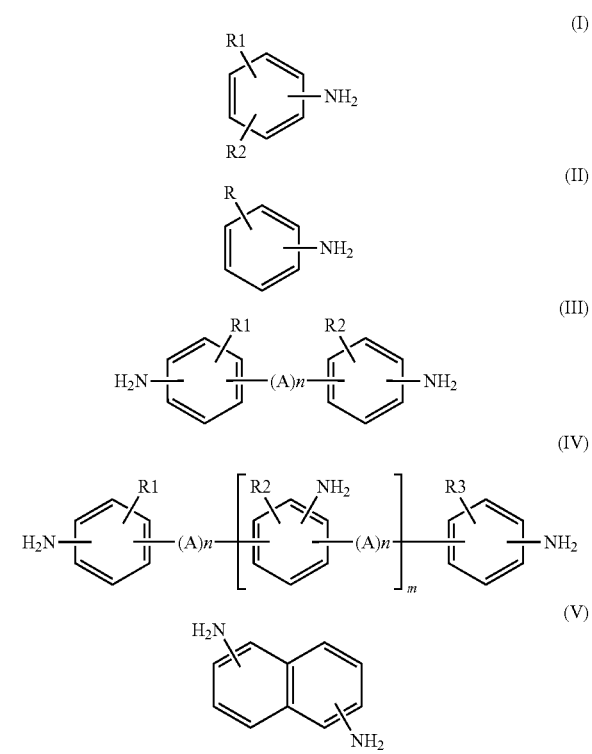

wherein:
each R, R1, R2, R3 is independently hydrogen or a hydrocarbyl (preferably alkyl, cycloalkyl, aryl, alkylaryl, alkylene) or hydrocarbyloxy (preferably alkyloxy, cycloalkyloxy, aryloxy, alkylaryl-oxy, alkylene-oxy) group containing up to 8 carbon atoms, preferably up to 4 carbon atoms, A is a divalent hydrocarbon (i.e. alkyl, cycloalkyl, aryl, arylalkyl) group having from 1 to 10 carbon atoms, preferably from 1 to 6 carbon atoms, n has the value of zero or 1, when n is zero both aromatic rings are fused, m has the value of zero or any natural number of $\geq 1$.

In the process according to the invention also more than one of the aromatic amines represented by the general formulas (I), (II), (In (IV) and (V) may be reacted with an organic carbonate in the presence of $Zn_4O(OAc)_6$ as catalyst.

More preferably the aromatic amines are selected from the group consisting o-toluidine, m-toluidine, p-toluidine, 2,4-xylidine, 3,4-xylidine, 2,5-xylidine, 4-ethylaniline, 3-propylaniline, 1,2-diaminobenzene, 1,3-diaminobenzene, 1,4-diaminobenzene, 2,4-diaminotoluene (2,4-TDA), 2,6-diaminotoluene (2,6-TDA), technical mixtures of the two TDA isomers 2,4-TDA and 2,6-TDA (about 80/20 mixtures), 4,4'-diaminodiphenylmethane (4,4'-MDA), 2,4'-diaminodiphenylmethane (2,4'-MDA), 2,2'-diaminodiphenylmethane (2,2'-MDA), amines of the diphenylmethane series obtained by acid catalyzed condensation/rearrangement reaction of aniline and formaldehyde and containing mixtures of 4,4'-MDA, its isomers and higher homologues (usually referred to as MDA or PMDA), 1,5-diaminonaphtalene, o-anisidine, m-anisidine, p-anisidine and mixtures thereof.

Most preferably, the aromatic amine is selected from the group consisting of 2,4-diaminotoluene (2,4-TDA), 2,6-aminotoluene (2,6-TDA), technical mixtures of the two TDA isomers 2,4-TDA and 2,6-TDA (about 80/20 mixtures), 4,4'-diaminodiphenylmethane (4,4'-MDA), 2,4'-diaminodiphenylmethane (2,4'-MDA), 2,2'-diaminodiphenylmethane (2,2'-MDA), amines of the diphenylmethane series obtained by acid catalyzed condensation/rearrangement reaction of aniline and formaldehyde and containing mixtures of 4,4'-MDA, its isomers and higher homologues (usually referred to as MDA or PMDA), 1,5-diaminonaphthalene.

Not only aromatic amines can be used as starting materials, other primary amines are suitable as well, like aliphatic mono-, di- and/or polyamines, mixed aliphatic-cycloaliphatic mono-, di- and/or polyamines, cycloaliphatic mono-, di- and/or polyamines. Specific but not limiting examples of such amines are methyl amine, ethyl amine, the isomers of propyl, butyl or pentyl amine and their higher homologues, ethylene diamine, 1,2-diamino propane, am-diamino alkanes like 1,3-diamino propane as well as higher homologues like e.g. 1,6-diamino hexane, substituted α,ω-diamino alkanes, cyclohexyl amine, substituted cyclohexylamines, the isomers of diamino cyclohexane, diamino cyclohexanes having substituents on the cycloaliphatic ring, the isomers of diamino dicyclohexylmethane, isophorone diamine, benzyl amine, 2-phenylethyl amine, 1-phenylethyl amine.

In one embodiment of the invention, the reaction is run using a single amine. In another embodiment, mixtures of two or more amines are used as starting material.

Dialkyl Carbonates

In the process of the invention suitable organic carbonates are cyclic and acyclic organic carbonates, and they are selected preferably from the group consisting of ethylene carbonate, propylene carbonate, styrene carbonate, dimethyl carbonate, diethyl carbonate, dipropyl carbonate, dibutyl carbonate, dihexyl carbonate, methyl ethyl carbonate, methyl butyl carbonate, diphenyl carbonate, methyl phenyl carbonate, and mixtures thereof.

More preferably the organic carbonate is selected from the group consisting of dimethyl carbonate and diethyl carbonate, and most preferably the organic carbonate is dimethyl carbonate $(Me)_2CO_3$.

The Catalyst

In the process of the invention the catalyst is $Zn_4O(OAc)_6$, also called basic zinc acetate or hexakis(μ-acetate)-μ-oxatetrazinc. For the avoidance of doubt the functional group Ac— refers to the formula $CH_3$—CO—. This catalyst may be prepared by different methods. For example, sublimation of zinc acetate hydrate according to the method disclosed in the article Gordon et al., Canadian Journal of Chemistry, 1982, 61, 1218, or by reaction of Zn metal with acetic acid and hydrogen peroxide as disclosed in the European patent EP-A-0049671. Industrial and Engineering Chemistry Research, 22 (1983), 380-381 describes the synthesis of $Zn_4O(OAc)_6$ from reaction of zinc oxide with acetic acid. Inorganica Chimica Acta, 181 (1991), 285-289 propose the same reaction but using $CCl_4$ as solvent. Boiling zinc acetate dehydrate in ethanol has also been described as method to prepare $Zn_4O(OAc)_6$ in The Journal of Physical Chemistry B (2003), 107, 568-574.

The Process

In the process of the invention the aromatic amine and the organic carbonate are reacted in the presence of the tetranuclear zinc catalyst.

The reaction is preferably conducted at a temperature of from 80° C. to 250° C., more preferably from 100° C. to 230° C., and most preferably from 150° C. to 220° C. If the temperature is too low, the reaction rate might be reduced too much; while at a too high reaction temperature, the risk of unwanted side reaction significantly reducing yield and/or selectivity will increase.

The pressure of the process is the autogenous pressure developing at the chosen reaction temperature. Alternatively, the pressure can also be modified or adjusted by adding a gas inert under the reaction conditions, which can be selected from, but is not limited to, nitrogen, a noble gas, carbon dioxide, or mixtures of the aforesaid compounds, to the reaction mixture. Preferably, the absolute pressure is about 1-50 bar, more preferably about 1-40 bar, even more preferably 2-30 bar, and most preferably about 3-25 bar.

The reaction time depends on the other reaction conditions and can be determined in orienting experiments. Typically, the reaction time is less than or equal to 12 hours, preferably less than or equal to 10 hours, more preferably 1-6 hours, and most preferably 2-4 hours.

The reaction preferably is conducted under conditions at which none of the reactants or products undergoes decomposition.

The reactants can preferably be employed in an equimolar basis or one reactant may be present in an excess with respect to the other.

In a preferred embodiment, the reactant in excess is the organic carbonate with respect to the aromatic amine. In that case the excess of organic carbonate may be recovered easily once the reaction is finished.

Usually, the molar ratio of organic carbonate to primary amino groups originating from the aromatic amine is 1:1-50, preferably 1:1-40, more preferably 1:5-35, even more preferably 1:7-30, and most preferably 1:10-25.

The quantity of catalyst employed usually depends upon the aromatic amine and the reaction conditions. The quantity of catalyst employed is described based on the zinc content of the catalyst and the primary amino groups originating from the aromatic amine and usually is 0.001-10 mol zinc per 100 mols of primary amino groups (that is 0.001-10 mol % based on the primary amino groups), preferably 0.005-8 mol zinc per 100 mols of primary amino groups, more preferably 0.01-5 mol zinc per 100 mols of primary amino groups, and most preferably 0.05-3 mol zinc per 100 mols of primary amino groups. Of course, higher amounts of catalyst can be applied as well if considered appropriate. Higher amounts of catalyst can locally be present in the reactor if considered appropriate.

According to this invention, the process can be run with or without the usage of an additional solvent.

According to a preferred embodiment of this invention, the process can be run without the usage of an additional solvent. In this case, the excess of dialkyl carbonate serves as solvent.

According to another preferred embodiment of this invention, the process is run in the presence of an additional solvent. The expression additional solvent includes the usage of a single additional solvent as well as of a mixture of two or more additional solvents. A wide variety of compounds can be applied as solvent. Aliphatic and aromatic hydrocarbons and their halogenated derivatives are suitable solvents like benzene, toluene, the isomers of xylene, ethylbenzene, chlorobenzene, the isomers of dichlorobenzene, ether, etc.

Examples of classes of suitable polar solvents include, but are not limited to, ketones, amides, sulfoxides, sulfones, ionic liquids. Specific examples include, but are not limited to, acetone, butanone, dimethylformamide, dimethyl sulfone, dimethyl sulfoxide, 1-octyl-3-methylimidazolium tetrafluoroborate ($[C_8$-mim$]BF_4$), 1-butyl-3-methylimidazolium tetrafluoroborate ($[C_4$-mim$]BF_4$), 1-butyl-3-methylimidazolium tetrafluorophosphate ([bmim]$BF_4$), 1-butyl-3-methylimidazolium hexafluorophosphate ([bmim]$BF_6$) and so on.

According to another preferred embodiment of this invention, the process is run in the presence of a hydroxyl component R—OH as solvent. In this case, the process is preferably run in the presence of a hydroxyl component R—OH as solvent where the organic group R of said hydroxyl component R—OH is the same as in the dialkyl carbonate applied as reactant. Apart from being solvent to conveniently facilitate the reaction, the presence of said hydroxyl components R—OH can support depressing side-reactions and improving product selectivity. The hydroxyl component R—OH is selected preferably from the group consisting of ethylene glycol, propylene glycol, styrene glycol, methanol, ethanol, propanol, butanol, hexanol, phenol, and mixtures thereof. Preferably, the hydroxyl component R—OH is chosen to match the hydroxyl component R—OH which is liberated during the reaction of the aromatic amine and the organic carbonate.

The reaction can be carried out continuously, semi-continuously or batch-wise. The order of the addition of the raw materials and/or the catalyst to the reactor is not critical, and the best way and/or most advantageous order to add the material and catalyst can be determined in orienting experiments. Furthermore, the hydroxyl component R—OH formed during the reaction can be removed from the reactor by appropriate means continuously or intermittently to shift the reaction equilibrium to the product side.

Appropriate reactors include, but are not limited to, stirred reactors, tubular reactors with or without inserts, tubular reactors with or without mixing elements, tubular reactors with or without redispersing elements, tubular reactors with a combination of two or more members of the group including inserts, mixing elements and redispersing elements, reaction columns, or an appropriate combination of different reactors.

The resulting reaction mixture is removed from the reactor. The process of work-up and/or product isolation can be achieved by means of any appropriate technique/means/process step. Appropriate techniques/means/process steps include, but are not limited to, distillation, crystallization, filtration, sedimentation, decantation, centrifugation, extraction, separation applying a membrane process, or other means or by combination of two or more of the aforesaid techniques/means.

Similarly, the catalyst can be recovered and reused in the process by means of any appropriate technique/means/process step. Appropriate techniques/means/process steps include, but are not limited to, distillation, crystallization, filtration, sedimentation, decantation, centrifugation, extraction, separation applying a membrane process, or other means or by combination of two or more of the aforesaid techniques/means.

As described, starting materials, intermediates, solvents and/or catalysts can be recovered and rerouted to any process step considered appropriate.

Surprisingly, it has been found that the reaction of aromatic amines and organic carbonates using $Zn_4O(OAc)_6$ as catalyst allows the preparation of aromatic carbamates with high yield and selectivity. The amount of N-alkylated byproducts is low (usually not higher than 2%). Additionally, the induction period to initiate the reaction is significantly reduced in comparison with prior art catalysts.

The carbamates obtained in the process according to the invention are then preferably used in the process for the production of the respective isocyanates. Preferably the isocyanates are obtained by thermal treatment of the carbamates (e.g. 50-300° C. for at least 1 min to 3h). The present invention is, thus, also directed to a process for the production of isocyanates wherein in a first step aromatic carbamates are produced by reaction of an aromatic amine with an organic carbonate in the presence of $Zn_4O(OAc)_6$ as catalyst and wherein in a second step the carbamate obtained in the first step is then subjected to thermal treatment (preferably 50-300° C. for at least 1 min to 3h).

DESCRIPTION OF THE FIGURES

FIG. 1 represents the structure of the tetranuclear cluster $Zn_4O(OAc)_6$ as described by Hiltunen et al., in Acta Chemica Scandinavica A, 1987, 41, 548. In that tetranuclear cluster, each zinc atom is tetrahedrally coordinated by four oxygen atoms, three from different bidentate acetate groups and the fourth being from a central oxygen.

Figure 2:
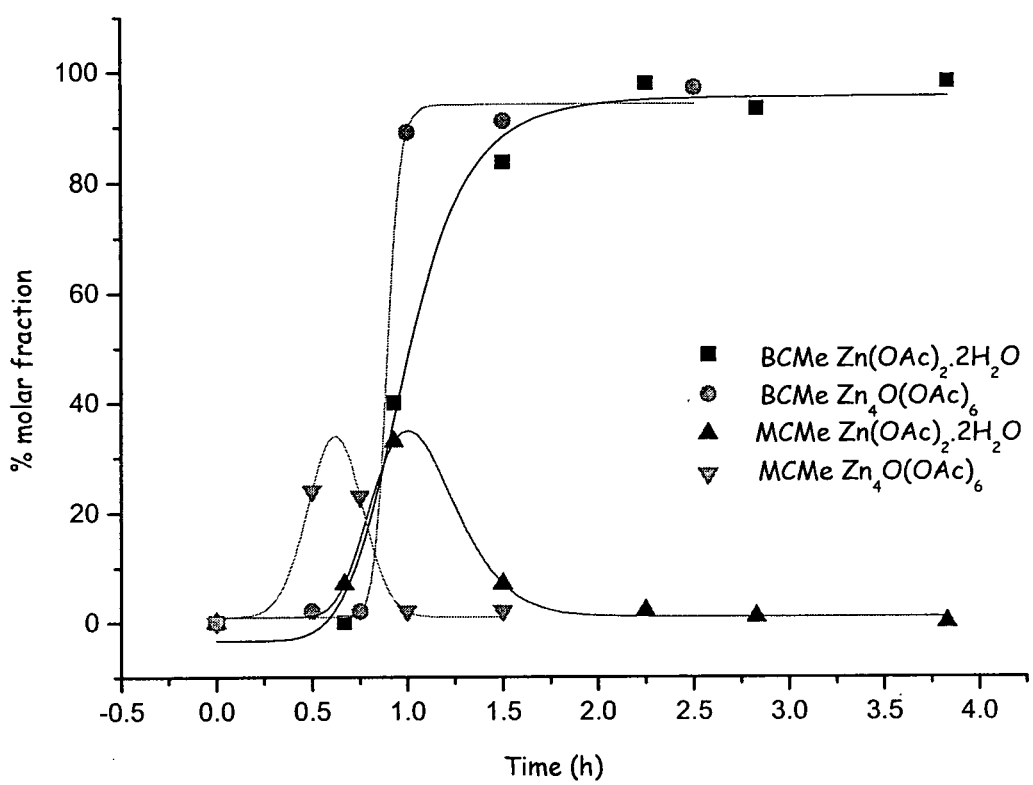

FIG. 2 shows the curves of formation of mono- and biscarbamates in the reaction of MDA with dimethyl carbonate in the presence of either $Zn4O(OAc)_6$ or zinc acetate dihydrate as catalyst according to Example 1 (according to the invention) and the Comparative example. It is observed that the mono- and biscarbamates are formed earlier and with a steeper slope when $Zn_4O(OAc)_6$ is used as catalyst if compared with zinc acetate dihydrate. The yields of the final product are in both cases very similar. The following signs are used in FIG. 2:

| Sign | Species |
| --- | --- |
| ▲ | % molar fraction of the monocarbamate obtained using zinc acetate dihydrate as catalyst (MCME $Zn(OAc)_2 \cdot 2H_2O$) |
| ▼ | % molar fraction of the monocarbamate obtained using $Zn_4O(OAc)_6$ as catalyst (MCME $Zn_4O(OAc)_6$) |
| ■ | % molar fraction of the biscarbamate obtained using zinc acetate dihydrate as catalyst (BCME $Zn(OAc)_2 \cdot 2H_2O$) |
| ● | % molar fraction of the biscarbamate obtained using $Zn_4O(OAc)_6$ as catalyst (BCME $Zn_4O(OAc)_6$) |

EXAMPLES

Dimethyl carbonate (99% purity) and diethyl carbonate (99% purity) were purchased from Aldrich and were dried with 4 Å molecular sieves. Water content analysis of the organic carbonates (Karl Fischer) was performed and water concentration was always under 30 ppm.

Aniline (99% purity), 2,4-diaminotoluene (98% purity), 4,4'-diaminodiphenylmethane (97% purity), and $Zn(OAc)_2 \cdot 2H_2O$ (99% purity) were purchased from Aldrich and were used without further purification.

Preparative Example

Preparation of the Catalyst Zn4O(OAc)6

Basic zinc acetate, $Zn_4O(OAc)_6$ was prepared according to the process described in Gordon et al., Canadian Journal of Chemistry, 1982, 61, 1218.

Zinc acetate hydrate, 99% purity, was heated at 250° C. and approximately 0.08 mbar during 6 hours to obtain a sublimated solid.

The catalyst obtained by sublimation was further characterized by elemental analysis. The calculated values for $C_{12}H_{18}O_{13}Zn_4$ are 22.81% C and 2.87% H, and it was found 23.02% C and 2.87% H.

Example 1

Preparation of a Carbamate Derived from MDA and DMC 0.5 g (2.45 mmol) of 4,4'-diphenylmethanediamine (MDA), 5.6 g (61 mmol) of dimethyl carbonate, and 3.9 mg of $Zn_4O(OAc)_6$ (0.0061 mmol, 0.25 mol % referred to MDA or 0.125 mol % based on the amino groups present) prepared in the Preparative Example, were placed with a magnetic stirrer in a Teflon vessel in a 25 mL autoclave.

The atmosphere was purged with nitrogen and then the autoclave was pre-heated until reaching an internal temperature of 180° C. (approx. 40 min), the mixture was then maintained at this temperature for 2 hours. Autogenous pressure generated at 180° C. is 8 bar. The mixture was stirred at 810 rpm.

Then the autoclave was removed from the heating mantle, and it was allowed to cool at room temperature for 30 minutes, and afterwards in an ice-water bath.

The conversion of MDA and the yield of the products were determined by HPLC using calibration curves.

MDA conversion was higher than 99%, obtaining 97% yield of the biscarbamate, 1% yield of the monocarbamate and less than 1% of N-alkylated products.

Examples 2 to 7

Preparation of Carbamates Derived from MDA and DMC Using different amounts of reagents and catalysts In those examples were prepared aromatic carbamates derived from MDA and DMC following the process disclosed in Example 1 and using different amounts of reagents and of $Zn_4O(OAc)_6$ as catalyst. Internal temperature was 180° C., pre-heating time was 40 minutes, and the reaction time was 2 h in Examples 2 to 6, and 4h 20 min in Example 7. Autogenous pressure generated at 180° C. is 8 bar.

Table I shows the amounts used of MDA, DMC and $Zn_4O(OAc)_6$ as catalyst, and the yield of biscarbamate:

TABLE 1

| Example | MDA (mmol) | DMC (mmol) | Molar ratio DMC/MDA | Catalyst (mmol) | mol % of catalyst referred to MDA | mol % of Zn centres referred to MDA | mol % of Zn centres based on the amino groups present | Bis-Carbamate Yield (%) |
|---|---|---|---|---|---|---|---|---|
| 2 | 2.45 | 49 | 20 | 0.0061 | 0.25 | 1 | 0.5 | 95 |
| 3 | 2.28 | 37 | 16 | 0.0057 | 0.25 | 1 | 0.5 | 95 |
| 4 | 2.63 | 33 | 12.5 | 0.0066 | 0.25 | 1 | 0.5 | 74 |
| 5 | 2.55 | 64 | 25 | 0.0032 | 0.125 | 0.5 | 0.25 | 95 |
| 6 | 5.64 | 141 | 25 | 0.0035 | 0.0625 | 0.25 | 0.125 | 77 |
| 7 | 5.64 | 141 | 25 | 0.0035 | 0.0625 | 0.25 | 0.125 | 92 |

It is apparent from Table I that the use of the catalyst of the invention allows the preparation of biscarbamates in high yield, even at low catalyst concentration.

Examples 2 and 6 were repeated three times and the mean values of the yields were 97%±0% and 95%±1% respectively, showing a good repeatability.

Example 8

Preparation of a Carbamate Derived from MDA and DEC 0.4 g (2 mmol) of 4,4'-diphenylmethanediamine (MDA), 5.8 g (49 mmol) of diethyl carbonate, and 12.5 mg of $Zn_4O(OAc)_6$ (0.0196 mmol, 1 mol % referred to MDA or 0.5 mol % based on the amino groups present) prepared in the Preparative Example, were placed with a magnetic stirrer in a Teflon vessel in a 25 mL autoclave.

The atmosphere was purged with nitrogen and the autoclave was pre-heated until reaching an internal temperature of 180° C. (approx. 30 min), and the mixture was maintained at this temperature for 2 hours. The mixture was stirred at 810 rpm. Autogenous pressure generated at 180° C. is 5 bar.

Then the autoclave was removed from the heating mantle, and it was allowed to cool at room temperature for 30 minutes, and afterwards in an ice-water bath.

The conversion of MDA and the yield of the products were determined by HPLC using calibration curves.

MDA conversion was higher than 99%, and it was obtained 97% yield of the biscarbamate and less than 1% of N-alkylated products. Monocarbamate was not detected.

Example 9

Preparation of a Carbamate Derived from TDA and DMC 0.62 g (5 mmol) of 2,4-toluenediamine (TDA), 11.3 g (125 mmol) of dimethyl carbonate, and 19.8 mg of $Zn_4O(OAc)_6$ (0.031 mmol, 0.625 mol % referred to TDA or 0.3125 mol % based on the amino groups present) prepared in the Preparative Example, were placed with a magnetic stirrer in a Teflon vessel in a 25 mL autoclave.

The atmosphere was purged with nitrogen and the autoclave was pre-heated until reaching an internal temperature of 190° C. (approx. 60 min), and the mixture was maintained at this temperature for 2 hours. The mixture was stirred at 810 rpm. Autogenous pressure generated at 180° C. is 10 bar.

Then the autoclave was removed from the heating mantle, and it was allowed to cool at room temperature for 30 minutes, and afterwards in an ice-water bath.

The conversion of TDA and the yield of the products were determined by HPLC using calibration curves.

The conversion was higher than 99%, and it was obtained a 98% yield of the biscarbamate, 1% yield of the monocarbamate, and less than 1% of N-alkylated products.

Example 10

Preparation of a Carbamate Derived from TDA and DEC 0.45 g (3.64 mmol) of 2,4-toluenediamine (TDA), 10.9 g (91 mmol) of diethyl carbonate, and 14.3 mg of $Zn_4O(OAc)_6$ (0.0227 mmol, 0.625 mol % referred to TDA or 0.3125 mol % based on the amino groups present) prepared in the Preparative Example, were placed with a magnetic stirrer in a Teflon vessel in a 25 mL autoclave.

The atmosphere was purged with nitrogen and the autoclave was pre-heated until reaching an internal temperature of 190° C. (approx. 55 and the mixture was maintained at this temperature for 4 hours. The mixture was stirred at 810 rpm. Autogenous pressure generated at 180° C. is 8 bar.

Then the autoclave was removed from the heating mantle, and it was allowed to cool at room temperature for 30 minutes, and afterwards in an ice-water bath.

The conversion of TDA and the yield of the products were determined by HPLC using calibration curves.

The conversion was higher than 99%, and it was obtained a 97% yield of the biscarbamate, 2% yield of the monocarbamate, and less than 1% of N-alkylated products.

Example 11

Preparation of a Carbamate Derived from Aniline and DMC 0.48 g (5.1 mmol) of aniline, 11.6 g (128 mmol) of dimethyl carbonate, and 8.2 mg of $Zn_4O(OAc)_6$ (0.0129 mmol, 0.25 mol % referred to aniline or the amino groups present) prepared in the Preparative Example, were placed with a magnetic stirrer in a Teflon vessel in a 25 mL autoclave.

The atmosphere was purged with nitrogen and the autoclave was pre-heated until reaching an internal temperature of 180° C. (approx. 40 min), and the mixture was maintained at this temperature for 2 hours. The mixture was stirred at 810 rpm. Autogenous pressure generated at 180° C. is 8 bar.

Then the autoclave was removed from the heating mantle, and it was allowed to cool at room temperature for 30 minutes, and afterwards in an ice-water bath.

The conversion of aniline and the yield of the products were determined after purifying the raw product with a silica gel column, using a mixture of hexane/ethyl acetate (90/10 v/v) as eluents.

Aniline conversion was higher than 99%, and it was obtained a 96% yield of the carbamate.

Example 12

Preparation of a Carbamate Derived from Aniline and DEC 0.48 g (5.1 mmol) of aniline, 15.2 g (128 mmol) of diethyl carbonate, and 16.3 mg of $Zn_4O(OAc)_6$ (0.0255 mol, 0.5 mol % referred to aniline or the amino groups present) prepared in the Preparative Example, were placed with a magnetic stirrer in a Teflon vessel in a 25 mL autoclave.

The atmosphere was purged with nitrogen and the autoclave was pre-heated until reaching an internal temperature of 180° C. (approx. 30 min), and the mixture was maintained at this temperature for 2 hours. The mixture was stirred at 810 rpm. Autogenous pressure generated at 180° C. is 5 bar.

Then the autoclave was removed from the heating mantle, and it was allowed to cool at room temperature for 30 minutes, and afterwards in an ice-water bath.

The conversion of aniline and the yield of the products were determined after purifying the raw product with a silica gel column, using a mixture of hexane/ethyl acetate (90/10 v/v) as eluents.

Aniline conversion was higher than 99%, and it was obtained a 91% yield of the carbamate.

Comparative Example

Preparation of a Carbamate Derived from MDA and DMC Using Zinc Acetate Dihydrate as Catalyst 0.56 g (2.74 mmol) of 4,4'-diphenylmethanediamine (MDA), 6.2 g (69 mmol) of dimethyl carbonate, and 6.1 mg of zinc acetate dihydrate (0.0247 mmol, 1 mol % referred to MDA or 0.5 mol % based on the amino groups present), were placed with a magnetic stirrer in a Teflon vessel in a 25 mL autoclave.

The atmosphere was purged with nitrogen and the autoclave was pre-heated until reaching an internal temperature of 180° C. (approx. 40 min), and the mixture was maintained at this temperature for 2 hours. The mixture was stirred at 810 rpm. Autogenous pressure generated at 180° C. is 8 bar.

Then the autoclave was removed from the heating mantle, and it was allowed to cool at room temperature for 30 minutes, and afterwards in an ice-water bath.

The conversion of MDA and the yield of the products were determined by HPLC using calibration curves.

MDA conversion was higher than 99%, and it was obtained 98% yield of the biscarbamate, 1% yield of the monocarbamate, and less than 1% of N-alkylated products.

The invention claimed is:

1. A process for preparing aromatic carbamates which comprises reacting an aromatic amine with an organic carbonate in the presence of a catalyst, wherein the catalyst comprises $Zn_4O(OAc)_6$.

2. The process according to claim 1, wherein the aromatic amine is selected from the group consisting of aromatic amines represented by the general formulas (I), (II), (III), (IV) and (V):

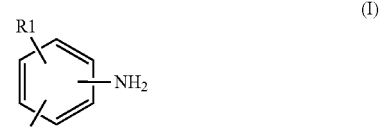

(I)

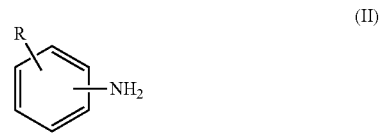

(II)

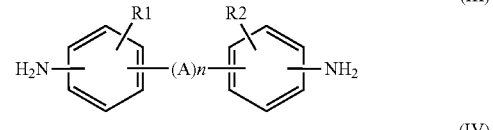

(III)

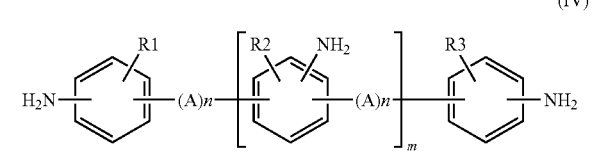

(IV)

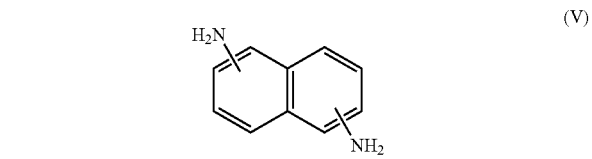

(V)

wherein:
R, R1, R2, R3 represents, independently of one another, hydrogen or a hydrocarbyl or hydrocarbyloxy group comprising up to 8 carbon atoms, A represents a divalent hydrocarbon group having from 1 to 10 carbon atoms, n is zero or 1, and when n is zero both aromatic rings are fused, and m is zero or any integer greater than or equal to 1.

3. The process according to claim 2, wherein R, R1, R2, R3 represents, independently of one another, hydrogen or a hydrocarbyl or hydrocarbyloxy group comprising up to 4 carbon atoms.

4. The process according to claim 2, wherein A represents a divalent hydrocarbon group having from 1 to 6 carbon atoms.

5. The process according to claim 2, wherein the aromatic amine is selected from the group consisting of aniline, o-toluidine, m-toluidine, p-toluidine, 2,4-xylidine, 3,4-xylidine, 2,5-xylidine, 4-ethylaniline, 3-propylaniline, 1,2-diaminobenzene, 1,3-diaminobenzene, 1,4-diaminobenzene, 2,4-diaminotoluene, 2,6-diaminotoluene, technical mixtures of 2,4-diaminotoluene and 2,6-diaminotoluene, 4,4'-diaminodiphenylmethane, 2,4'-diaminodiphenylmethane, 2,2'-diaminodiphenylmethane, amines of the diphenylmethane series obtained by acid catalyzed condensation and/or rearrangement reaction of aniline and formaldehyde and containing mixtures of 4,4'-diaminodiphenylmethane, its isomers and higher homologues, 1,5-diaminonaphtalene, o-anisidine, m-anisidine, p-anisidine and mixtures thereof.

6. The process according to claim 5, wherein the aromatic amine is selected from the group consisting of 2,4-diaminotoluene, 2,6-diaminotoluene, technical mixtures of 2,4-diaminotoluene and 2,6-diaminotoluene, 4,4'-diaminodiphenylmethane, 2,4'-diaminodiphenylmethane, 2,2'-diaminodiphenylmethane, amines of the diphenylmethane series obtained by acid catalyzed condensation and/or rearrangement reaction of aniline and formaldehyde and containing mixtures of 4,4'- diaminodiphenylmethane, its isomers and higher homologues, and 1,5-diaminonaphthalene.

7. The process according to claim 1, wherein the organic carbonate is selected form the group consisting of ethylene carbonate, propylene carbonate, styrene carbonate, dimethyl carbonate, diethyl carbonate, dipropyl carbonate, dibutyl carbonate, dihexyl carbonate, methyl ethyl carbonate, methyl butyl carbonate, diphenyl carbonate, methyl phenyl carbonate, and mixtures thereof.

8. The process according to claim 7, wherein the organic carbonate is selected from the group consisting of dimethyl carbonate and diethyl carbonate.

9. The process according to claim 8, wherein the organic carbonate is dimethyl carbonate.

10. The process according to claim 1, wherein the reaction is conducted at a temperature of from 80° C. to 250° C.

11. The process according to claim 1, wherein the reaction time is less than or equal to 12 hours.

12. The process according to claim 1, wherein the absolute process pressure is about 1-50 bar.

13. The process according to claim 1, wherein the molar ratio of organic carbonate to primary amino groups originating from the aromatic amine is 1:1-50.

14. The process according to claim 1, wherein the quantity of the catalyst is 0.001-10 mol zinc per 100 mols of primary amino groups.

15. A process for the production of isocyanates wherein in a first step aromatic carbamates are produced by reaction of an aromatic amine with an organic carbonate in the presence of Zn4O(OAc)6 as catalyst, and wherein in a second step the carbamate obtained in the first step is then subjected to thermal treatment.

16. The process according to claim 15, wherein the thermal treatment comprises exposure of the carbamate in the second step to a temperature of 50° C. to 300° C. for at least 1 min to 3 h.

* * * * *